(12) United States Patent
Delprat et al.

(10) Patent No.: US 10,639,384 B2
(45) Date of Patent: May 5, 2020

(54) TARGETING THE NEURONAL CALCIUM SENSOR 1 FOR TREATING WOLFRAM SYNDROME

(71) Applicants: INSERM (INSTITUT NATIONAL DE LA SANTÉ ET DE LA RECHERCHE MÉDICALE), Paris (FR); UNIVERSITÉ DE MONTPELLIER, Montpellier (FR)

(72) Inventors: Benjamin Delprat, Montpellier (FR); Cécile Cribaillet-Delettre, Montpellier (FR); Claire Angebault, Montpellier (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 16/086,861

(22) PCT Filed: Mar. 23, 2017

(86) PCT No.: PCT/EP2017/056940
§ 371 (c)(1),
(2) Date: Sep. 20, 2018

(87) PCT Pub. No.: WO2017/162798
PCT Pub. Date: Sep. 28, 2017

(65) Prior Publication Data
US 2019/0099502 A1    Apr. 4, 2019

(30) Foreign Application Priority Data

Mar. 23, 2016   (EP) .................... 16305330

(51) Int. Cl.
| | | |
|---|---|---|
| *A61K 48/00* | (2006.01) | |
| *A61K 38/17* | (2006.01) | |
| *A61P 3/10* | (2006.01) | |
| *A61P 7/12* | (2006.01) | |
| *A61P 27/00* | (2006.01) | |
| *A61K 9/51* | (2006.01) | |
| *C12Q 1/6883* | (2018.01) | |

(52) U.S. Cl.
CPC ............ *A61K 48/0066* (2013.01); *A61K 9/51* (2013.01); *A61K 38/17* (2013.01); *A61P 3/10* (2018.01); *A61P 7/12* (2018.01); *A61P 27/00* (2018.01); *C12Q 1/6883* (2013.01)

(58) Field of Classification Search
None
See application file for complete search history.

(56) References Cited

FOREIGN PATENT DOCUMENTS

| | | |
|---|---|---|
| EP | 1 250 931 A1 | 10/2002 |
| GB | 2 377 635 A | 1/2003 |
| WO | 00/18787 A1 | 4/2000 |
| WO | 2007/031727 A2 | 3/2007 |
| WO | 2014/049366 A1 | 4/2014 |

OTHER PUBLICATIONS

Benbow et al. Protection of Neuronal Calcium Sensor 1 Protein in Cells Treated With Paclitaxel. Journal of Biological Chemistry, 2011. 286 (40):34575-34582.*
Database WPI, Week 200143, Thomson Scientific, London, GB. Database Biosis [Online] Biosciences Information Service, Phildelphia, PA, US; Oct. 2003, Cryns Kim et al: "Mutational spectrum of the WFS1 gene in Wolfram syndrome, nonsyndromic hearing impairment, diabetes mellitus, and psychiatric disease."

* cited by examiner

*Primary Examiner* — Christopher M Babic
*Assistant Examiner* — Kimberly A. Aron
(74) *Attorney, Agent, or Firm* — W&C IP

(57) ABSTRACT

The present invention relates to novel therapeutic ways for treating Wolfram Syndrome (WS) by targeting the neuronal calcium sensor 1 (NCS1). The present inventors have demonstrated that WFS1, which loss of function is responsible of the Wolfram Syndrome, forms a complex with the neuronal calcium sensor 1 (NCS1). The inventors have further demonstrated that WFS1 associates with NCS1 to prevent its degradation by the proteasome and that NCS1 regulates VDAC expression and mitochondrial respiratory chain. Thus, present invention provides an agonist of NCS1 for use in the treatment of WS. Such an agonist is e.g. a NCS1-encoding polynucleotide, an inhibitor of the proteasome or of calpains. The inventors have further shown that overexpression of NCS1 in WS cells allows increasing complex II driven respiration. The present invention further relates to a method for predicting the severity of WS by measuring the NCS1 level in a sample obtained from a patient.

1 Claim, 4 Drawing Sheets

A

B

C

D

TARGETING THE NEURONAL CALCIUM SENSOR 1 FOR TREATING WOLFRAM SYNDROME

FIELD OF THE INVENTION

The present invention relates to novel therapeutic ways for treating Wolfram Syndrome.

BACKGROUND OF THE INVENTION

Wolfram Syndrome (WS or DIDMOAD) is an autosomal recessive neurodegenerative disorder characterized by diabetes insipidus (DI), diabetes mellitus (DM), optic atrophy (OA) and deafness (D). There are two types of Wolfram Syndrome, type 1 and type 2. The type 1 (WS1), the most common, is caused by a mutation in the WFS1 gene which encodes wolframin, a transmembrane protein located in the endoplasmic reticulum (ER). Wolframin plays a role in ER calcium homeostasis and in several protein responses. This protein is abundantly expressed in the pancreas, brain, heart and muscle (Rigoli. L and Di Bella. C, *Curr Opin Pediatr.* 2012; 24(4):512-7). Mutations in the WFS1 gene leads to a partially/totally inactivated wolframin which results in the development of endoplasmic reticulum stress, leading to apoptosis.

The morbidity and mortality in WS1 are very high and the median age of death is around 30. WS1 usually occurs in the first decade of life with the apparition of a diabetes mellitus type 1 and an optic atrophy. 50% of patients also develop diabetes insipidus and present some degree of deafness. Around 65% of the patients develop the whole four DIDMOAD symptoms. Some patients additionally present neurological abnormalities (62% of the patients) such as ataxia of the trunk, urinary tract abnormalities (urinary incontinence, recurrent infections, hydroureter) gastrointestinal tract affections (such as bowel dismotility) and primary hypogonadism. Around 60% of the patients are affected by severe episodes of depression, psychosis, or organic brain syndrome as well as impulsive verbal and physical aggression. Magnetic resonance imaging scans demonstrate generalized brain atrophy, especially in the cerebellum, medulla, and pons; absence of signal from the posterior pituitary; and reduced signal from the optic nerve (Ito S et al., *AJNR Am J Neuroradiol,* 2007; 28:305-306). Central apnea, due to bulbar dysfunction is a common cause of mortality in WS1 patients.

No treatment of Wolfram Syndrome is known to date. The management consists in treating the symptoms e.g. with insulin replacement and a controlled diet to treat diabetes mellitus, prophylactic antibiotherapy for preventing recurrent urinary tract infections.

Thus, there is a real need to develop novel and efficient therapies which would allow treating Wolfram Syndrome or at least reducing its symptoms.

DETAILED DESCRIPTION

The present inventors have discovered that WFS1, which loss of function is responsible of the Wolfram Syndrome, forms a complex with the neuronal calcium sensor 1 (NCS1) and further with inositol 1,4,5-triphosphate receptor 1 (ITPR1) and voltage-dependent anion channel 1 (VDAC1) to promote ER-mitochondrial Ca2+ transfer. The inventors have further demonstrated that WFS1 associates with NCS1 to prevent its degradation by the proteasome and that NCS1 regulates VDAC expression and mitochondrial respiratory chain.

As used herein, the expression "NCS1 encoding gene" refers to the neuronal calcium sensor 1 gene of any species to which the methods according to the invention can apply. Particularly, the NCS1 encoding gene is human. The human NCS1-encoding gene is also known as the "FREQ gene" localized on chromosome 9 at position 9q34.11 and is quite conserved between species (Bourne et al., *Journal of Biological Chemistry,* 276, 11949-11955). NCS1 is an EF-hand cytosolic protein preferentially expressed in neurons (Pongs et al., *Neuron,* 1993, 11, 15-28) and known to regulate inositol 1,4,5-triphosphate receptor (ITPR) (Nakao et al. PloS one 2015, 10, e0125050; Schlecker et al., *The Journal of clinical investigation,* 2006, 116, 1668-1674; Zhang et al., *Experimental eye research,* 2014, 125, 30-40) and Dopamine D2 receptor (Kabbani et al., *J. Neurosci,* 2002, 22, 8476-8486).

The expression "NCS1-encoding gene" should be understood broadly. In the context of the present invention, the NCS1-encoding gene can have the exact same sequence as the above-mentioned FREQ gene or can be any functional variant thereof. A functional variant of FREQ is a sequence that will produce a functional NCS1 protein. The skilled person knows how to select FREQ functional variants suitable for the purpose of the present invention. In the context of the present invention, a "functional NCS1 protein" means that NCS1 is capable of binding ITPR1 to promote ER-mitochondrial Ca2+ transfer. Thus, a suitable test for determining if NCS1 is "functional" in the context of the present invention consists in evaluating if said NCS1 is able 1/ to bind to ITPR1 and 2/ to promote the Ca2+ mitochondria uptake. A suitable test for detecting the NCS1/ITPR1 binding and the NCS1/ITPR1-mediated mitochondria Ca2+ uptake is disclosed in Example 1 of the pending application.

Typically, variants of the FREQ gene according to the invention present a sequence identity of at least 70%, 75%, 80% or more particularly 90% with the FREQ sequence.

As used herein, the percentage of sequence identity refers to comparisons between nucleic acid sequences, and is determined by comparing two optimally aligned sequences over a comparison window, wherein the portion of the nucleic acid sequence in the comparison window may comprise additions, deletions (i.e., gaps), or substitutions as compared to the reference sequence (which does not comprise additions, deletions or substitutions) for optimal alignment of the two sequences. The skilled person will know how to determine the percentage of identity between two nucleic acid sequences.

The "WFS1 gene" (gene bank ID: 7466) codes for wolframin, a predicted 890-amino acid transmembrane protein. It is located at position 4p16.1 in the human genome and its mutation(s) is(are) responsible of the Wolfram Syndrome of type 1. The following mutations of WFS1, which are identified by their rs reference in the NCBI dbSNP Short Genetic Variations Database, are examples of mutations known to cause Wolfram Syndrome 1: rs28937890, rs28937891, rs104893879, rs28937892, rs104893880, rs104893881, rs587776598, rs71524377. Most of the mutations associated with Wolfram syndrome are spread over the entire coding region and are typically inactivating (Cryns et al., *Hum. Mutat.,* 2003, 22: 275-287).

In the context of the invention, the term "treating" or "treatment", means reversing, alleviating, inhibiting the progress of, or preventing the disorder or condition to which such term applies, or one or more symptoms of such disorder or condition. A "therapeutically effective amount" is intended for a minimal amount of active agent (e.g., NCS1-encoding polynucleotide) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "subject" denotes a mammal, particularly a human.

Treatments of the Wolfram Syndrome According to the Invention

In a first aspect, the inventors have demonstrated that WFS1 interacts with NCS1 and modulates its expression. They have observed that the protein level of NCS1 was significantly reduced (of around 50%) in Wolfram patients cells due to an over-degradation of NCS1 by the proteasome. By interacting with NCS1, WFS1 also interacts with ITPR1, and thereby regulates the mitochondrial Ca2+ uptake.

Ca2+ is an important actor in several pathways of the mitochondrial function, particularly in the respiratory complexes. Patient cells presented a significant decrease (around 20%) in the expression of the complex II (SDHA) and complex III (UQCRC2) subunits. Accordingly, Wolfram syndrome induces a loss of mitochondrial proteins, thereby impairing the mitochondrial function.

The inventors have demonstrated that the overexpression of NCS1 is able to significantly increase the complex II respiration in Wolfram patient's cells, and is thus able to counter some effects of the WFS1 mutation.

Increasing/stimulating the expression of NCS1 is thus a very efficient pathway for treating Wolfram Syndrome.

Accordingly, in a first aspect, the present invention relates to an agonist of NCS1 for use in the treatment of Wolfram Syndrome.

An "agonist" of NCS1 should be understood broadly. In the context of the present invention an agonist is a compound which positively modulates the expression/activity of NCS1. Such a compound can be e.g.:
an agent stimulating the expression of NCS1 (methods for determining whether a compound increases or activates the expression of NCS1 are e.g. disclosed in U.S. Pat. No. 7,230,155);
an agent preventing the degradation of NCS1;
an agent mimicking NCS1's expression/activity; or
an agent stabilizing NCS1 interaction with WFS1; thereby preventing it routine to the proteasome.

In the context of the present invention, the effects of the agonist can be evaluated by measuring changes in the NCS-1 quantity, or by measuring the downstream effects of NCS-1 function, for example by measuring the complex II respiration.

Compounds Stimulating the Expression of NCS1
NCS1-Encoding Polynucleotide

In a first embodiment, the "agonist" according to the present invention is a NCS1-encoding polypeptide.

Thus, the present invention relates to a NCS1-encoding polynucleotide for use in the treatment of Wolfram Syndrome.

The present invention also provides a method for treating Wolfram Syndrome comprising administering, to a patient in need thereof, a NCS1-encoding polynucleotide Gene therapy is a particularly convenient way to treat Wolfram Syndrome as it enables the provision of an additional NCS1 polypeptide, for example as discussed below.

Gene therapy may be carried out by means of supplementation of cells lacking a functional NCS1 polypeptide with a functional NCS1. Production of a suitable gene product may be achieved using recombinant techniques. For example, a suitable vector may be inserted into a host cell and expressed in that cell.

Thus, the invention relates to a method for treating Wolfram Syndrome which comprises the step of administering in a subject in need thereof a NCS1-encoding polynucleotide, i.e. a nucleic acid sequence that encodes a functional NCS1, so that NCS1 is expressed in vivo by the cells of the subject that have been transfected with said polynucleotide. Accordingly, said method leads to an overexpression of wild-type NCS1 which compensates the deregulated over-degradation of NCS1 by the proteasome.

The invention also relates to the use of a NCS1-encoding polynucleotide for the manufacture of a medicament intended for the treatment of Wolfram Syndrome.

Said NCS1-encoding polynucleotide is administered in a therapeutically effective amount.

Preferably the NCS1 sequence according to the invention is associated with elements that enable for regulation of its expression, such as a promoter sequence.

Such a nucleic acid may be in the form of a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, lentiviruses and adeno-associated viruses (AAV)), which serve equivalent functions. Adeno-associated viral vectors have proven to be very useful for transferring gene-encoding polynucleotides to several tissues, such as retina (see Surace et al., *Vision Serach* 48, 353-359, 2008; Hellström et al., *Gene Therapy*, 16, 521-532, 2009; Cwerman-Thibault et al., *Molecular Therapy-Methods & Clinical Development* 2, 15003, 2015 or Bemelmans et al., PLoS ONE 8(4): e61618, 2013). Thus, in the context of the present invention, AAV vectors represent very promising tool for directly delivering the NCS1-encoding polynucleotide to tissues affected during WS, e.g. to the retina.

Accordingly, in a preferred embodiment, the viral vector is an adeno-associated virus vector.

Different types of AAV vectors can be used depending on the type of administration and on the tissue to be targeted. For instance, the AAV2 vector has proven to be particularly efficient when administered locally (e.g. by intra-ocular administration for targeting retina: see Surace et al, 2008;

Hellström et al., 2009; and Cwerman-Thibault et al., 2015), whereas the scAAV9 and 10 vectors are particularly efficient when administered systemically (Bemelmans et al, 2013).

The NCS1-encoding polynucleotide may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, microinjection, transduction, cell fusion, DEAE dextran, calcium phosphate precipitation, or use of a gene gun.

The NCS1-encoding polynucleotide can also be introduced ex vivo or in vivo by lipofection. In certain embodiments, the use of liposomes and/or nanoparticles is contemplated for the introduction of the donor nucleic acid targeting system into host cells.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core.

Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes (Felgner et al., 1989).

Alternatively, one of the simplest and the safest way to deliver the NCS1-encoding polynucleotide across cell membranes in vivo may involve the direct application of high concentration free or naked polynucleotides (typically mRNA or DNA). By "naked DNA (or RNA)" is meant a DNA (RNA) molecule which has not been previously complexed with other chemical moieties. Naked DNA uptake by animal cells may be increased by administering the cells simultaneously with excipients and the nucleic acid. Such excipients are reagents that enhance or increase penetration of the DNA across cellular membranes and thus delivery to the cells delivery of the therapeutic agent. Various excipients have been described in the art, such as surfactants, e.g. a surfactant selected form the group consisting of Triton X-100, sodium dodecyl sulfate, Tween 20, and Tween 80; bacterial toxins, for instance streptolysin 0, cholera toxin, and recombinant modified labile toxin of E coli; and polysaccharides, such as glucose, sucrose, fructose, or maltose, for instance, which act by disrupting the osmotic pressure in the vicinity of the cell membrane. Other methods have been described to enhance delivery of free polynucleotides, such as blocking of polynucleotide inactivation via endo- or exonucleolytic cleavage by both extra- and intracellular nucleases.

Knowing the sequence of the NCS1 gene (FREQ), one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides of the invention can be use in an isolated (e.g., purified) form or contained in a vector, such as a membrane or lipid vesicle (e.g. a liposome).

Activators of NCS1's Expression

In another embodiment, the NCS1 agonist is a compound which induces an activation/increase in the expression of the NCS1 gene (FREQ).

Such compounds can be chemical molecules or proteins that bind to the mRNA of a gene encoding a NCS-1 polypeptide, thereby stabilizing the native conformation of the mRNA and facilitating transcription and/or translation.

Calcium was shown to increase the expression of NCS1 (see Hamasaki-Katagiri et al, J Biol Chem. 2010 Feb. 12; 285(7):4405-14). This increase is prevented by FK506, a calcineurin inhibitor.

Inhibitors of NCS1+s Repression

In a further embodiment, the agonist according to the present invention can inhibit NCS1's repression, i.e. inhibit a repressor (inhibitor) of NCS1 expression.

Thus, in a particular embodiment, the NCS1 agonist according to the present invention inhibits the repressors of NCS1.

In this case, the NCS1's agonist may be based on antisense oligonucleotide constructs. Anti-sense oligonucleotides, including anti-sense RNA molecules and anti-sense DNA molecules, would act to directly block the translation of the inhibitor of NCS1 by binding thereto and thus preventing protein translation or increasing mRNA degradation, thus decreasing the level of the target inhibitor, and thus its NCS1 inhibiting activity. Methods for using anti-sense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also inhibit NCS1's inhibitors expression. In this case, their expression is reduced by contacting a subject or cell with a small double stranded RNA (dsRNA), or a vector or construct causing the production of a small double stranded RNA, such that their expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Compounds Preventing NCS1's Degradation

As disclosed above, WFS1 interacts with NCS1 and the NCS1 level is highly affected in Wolfram-patients cells.

WFS1 regulates NCS1 protein stability by protecting NCS1 from proteasomal degradation.

Thus, preventing the degradation of NCS1 can also represent a promising tool for treating Wolfram Syndrome.

Inhibitors of the Proteasome

The inventors have demonstrated that it is possible to increase the NCS1 level in patient cells by using an inhibitor of the proteasome. Accordingly, inhibiting the proteasome pathway in Wolfram patients is a very efficient way for treating Wolfram syndrome.

Thus, in another aspect, the agonist of NCS1 according to the present invention is an inhibitor of the proteasome.

By an "inhibitor of the proteasome", it is herein referred to a compound which has the ability to reduce or prevent the degradation of proteins by the proteasome.

As disclosed in Grigoreva et al. (Grigoreva et al., *Oncotarget*, 2015, 1-17), several pathways can be targeted for inhibiting the proteasome activity. The proteasome-degradation system involves different actors: proteins which are to be degraded by the proteasome are firstly ubiquitinated by the E1-E2-E3 ubiquitination enzymatic cascade. Once ubiquitinated, the proteins are then transferred to the proteasome for degradation. The proteasome, also kwon as 26S proteasome, is a multi-unit enzyme complex consisting in the association of a cylindrical 20S complex with one or two regulatory 19S complex(es). The 19S complex prepares the substrate protein for degradation in the 20S complex.

Accordingly, inhibitors of the proteasome can either target the ubiquitination pathway or the proteasome structure/activity itself (see Grigoreva et al; Pellom et al, *Clin. Cell Immunol.*, 2012, S5; and Liu et al, *Biochimica et Biophysica Acta* 1855, 2015, 50-60).

Inhibitors of the proteasome are well known by the skilled person (see e.g. Nalepa et al., *Nature Reviews*, 2006, 5596-613; Bedford et al., *Nature Reviews*, 2010, 10, 29-46; Liu et al., *Biochimica et Biophysica Acta* 1855, 2015, 50-60; Pellom Jr. et al., *Clin. Cell Immunol.*, 2012, S5 and Grigoreva et al., *Oncotarget*, 2015, 1-17).

The following list discloses a non-exhaustive number of known inhibitors of the proteasomic activity.

Metcalf et al (*Expert Opinion on Therapeutic Patents*, 2014, 24:4, 369-382) and Pevzner et al (*Expert Opinion on Drug Discovery*, 2013, 8:5, 537-568) review all the major proteasome inhibitors known to date.

Boronic-acid based inhibitors: Peptide boronates selectively target the proteasome. They bound with the N-terminal threonine residue of the proteasome by a non-covalent bound.

Examples are:
Bortezomib. (See e.g. Luker et al., *Nature medicine*, 2003, 9(7), 969-973 and Adams et al., *Cancer investigation*, 2004, 22(2), 304-311). It is one of the most well-known proteasome inhibitors;
Delanzomib (CEP-18770) (See e.g. Berkerset al., *Molecular pharmaceutics*, 2012, 9.5: 1126-1135);
Ixazomib (MLN9708) (See Kupperman et al., *Cancer Research*, 2010, 70:1970-1980).

Peptide epoxyketone: They contain an α,β-epoxyketone moiety that assists in the formation of of a morpholino adduct with the N-terminal threonine residue of the proteasome.

Examples are:
Carfilzomib (PR-171) (See J Kuhn et al., *Current cancer drug targets*, 2001, 11(3):285-295);
Oprozomib (ONX-0912) (See Hurchla et al., *Leukemia*, 2013, 27(2), 430-440);
Epoxomicin (See Hanada et al., *J. Antibiot.* 1992, 45, 1746-1752).

Peptide aldehydes: They act against serine and cysteine protease and bind to the proteasome via nucleophilic binding.

Examples are:
MG132 (See for instance Momose et al., *Bioscience, Biotechnology and Biochemistry*, 2005, 69:1733-1742 and Alexandrova et al., *Cell biochemistry and function*, 2008, 26(3):392-398);
Tyropeptin A (See e.g. Momose et al., 2005; Hines et al., *Chemistry and Biology*, 2008, 15:501-512 and Momose et al., *Bioscience, Biotechnology and Biochemistry*, 2002, 66:2256-2258);
Felutamide B (See e.g. Hines et al., *Chemistry and Biology*, 2008, 15:501-512).

Salinosporamide analogs: they inhibit the catalytic activity of the 20S subunit by forming a complex with it.

Examples are:
Salinosporamide A (Marizomib): (see Macherla et al., *J. Med. Chem.*, 2005, 48:3684-3687).

β-lactones:

Examples are:
Omuralide/clasto-lactacystin-βlactones: creates a covalent bound with the catalytic Thr1 of the 13S subunit of the proteasome. (See Smith et al., *Molecular Medecine*, 2002, 8:382-392 and Hasegawa et al., *Bioorganic & MedicinalChemistry letters*, 2008, 18:5668-5671).

Tea polyphenols and polyphenol derivatives such as the Flavonoid compound Epigallocatechin gallate, possess the ability to bind to the proteasome (See Nam et al., *J. Biol. Chem.*, 2001, 276:13322-13330).

Belactosin: This compound is a Streptomyces metabolite which has the ability to efficiently inhibit the 20S subunit activity (see Asai et al., *Biochem. Pharmacol.* 2004, 67, 227-234).

Tyropeptins such as TP-110, a tyropeptin A derivative, specifically inhibits the chymotrypsin-like activity of the 20S mammalian proteasome (See Momose et al., *Bioscience, Biotechnology and Biochemistry*, 2005, 69:1733-1742).

Syrbactins such as syringolins and glidobactins are considered as promising proteasome inhibitors (see Clerc et al., *Proc Nat Acad Sci*, 2009, 106(16), 6507-6512).

Vinyl Sulfone and vinyl ester-containing compounds: they inhibit the proteasome by forming a covalent bound with the catalytic THR1 residues of the proteosomal active sites (see Baldisserotto et al., *Bioorg Med Chem Lett*, 2009, 19(7), 1966-1969).

TMC-95A is a cyclic tripeptide which inhibits all three proteolytic activities of the proteasome by a non-covalent link (see Koguchi et al., *Chem Inform*, 2000, 31(26)).

Metal complexes containing gold, zinc, nickel or copper have also been shown to have proteasome-inhibiting properties (see e.g. Milacic et al., *Cancer Res*, 2006, 66(21), 10478-86; Cvek et al., *J. Med Chem*, 2008, 51(20), 6256-8 and Daniel et al., *Breast Cancer Res*, 2005, 7(6), R897-908).

As disclosed above, several inhibitors of the proteasome activity or of the ubiquitination pathway are known to date. The skilled person will know how to select a suitable inhibitor for the purpose of the present invention.

In a further aspect, the present invention relates to a method for treating Wolfram Syndrome comprising administering, to a patient in need thereof, a therapeutically effective amount of an inhibitor of the proteasome.

Calpain Inhibitors

Several studies have reported that NCS1 is also degraded by calpains (see e.g. Benbow et al. *The Journal of Biological Chemistry*, vol 286, 40, 34575-34582, 2011; Blachford et al., *Cell Calcium*, vol 46, 257-262, 2009 and Boehmerle et al, PNAS, vol. 104, 26, 11103-11108, 2007). Accordingly, inhibiting the calpain-mediated degradation of NCS1 also represents a promising way for treating WS, as it would help enhancing the NCS1 level in affected cells.

Thus, in a further aspect, the agonist of NCS1 according to the present invention is a calpain inhibitor.

Calpains are calcium-dependent non-lysosomal neutral cysteine proteases. As disclosed above, they have the ability to specifically target and cleave NCS1, thereby preventing its interaction with ITPR1 and the $Ca^{2+}$ intake resulting thereof. Boehmerle (Boehmerle, 2007), Blachford (Blachford, 2009) and Benbow (Benbow, 2011), have all demonstrated that calpain inhibition allowed recovering a physiological intra-cellular level of NCS1, thereby allowing the recovery of the ITPR1-$Ca^{2+}$ mediated signaling.

In the context of the present invention, "a calpain inhibitor" is a compound which has the ability to reduce or prevent the degradation of NCS1 by calpains.

The skilled person knows several compounds having this type of activity. Calpain inhibitors have already been disclosed for the treatment of various pathologies such as inflammatory bowel diseases (see e.g. WO2015/066212, WO2012001121, JP2013063953; JP2010006834; CN104083350). O Donkor et al (*Expert Opinion on Therapeutic Patents*, 21:5, 601-636, 2011 and *Expert Opinion on Therapeutic Patents*, 25:1, 17-31, 2015) and Siklos et al (*Acta Parmaceutica Sinica B*, 5:6, 506-519, 2015) review all the major calpain inhibitors known to date.

Among these compounds, one may cite the following compounds:

Non-peptide calpain inhibitors such as carboxamides (Lubisch et al., Bioorg Med Chem Lett., 10(19), 2187-91, 2000; Lee et al, Eur J Med Chem., 44(3), 1331-4, 2009; Kim et al., Eur J Med Chem., 46(5), 1721-8, 2011), Dihydroxy-chalcones (Baek et al., Bioorg Chem., 51, 24-30, 2013); α-mercaptoacrylates (Rasbach et al., J Med Chem. 8, 52(1), 181-188, 2009).

Peptidomimetic calpain inhibitors such as epoxysuccinate-based inhibitors (Schiefer et al., J Med Chem.; 56(15): 6054-6068, 2013), α-Helical inhibitors (Jo et al., *J Am Chem Soc.*, 24, 134(42), 17704-13, 2012), peptidomimetic macrocycles (Chen et al., Chem Biodivers., 9(11), 2473-84, 2012; Abell et al., Angew Chem Int Ed Engl. 48(8), 1455-8, 2009).

The inhibitor of the proteasome or of calpains according to the invention can be administered by any suitable route of administration. For example, the inhibitor according to the invention can be administered by oral (including buccal and sublingual) or parenteral (including intramuscular, intraarterial, intrathecal, subcutaneous and intravenous) administration. The skilled person will know which dosage and route of administration are the most adapted depending on the type of inhibitor selected.

In a further aspect, the present invention relates to a method for treating Wolfram Syndrome comprising administering, to a patient in need thereof, a therapeutically effective amount of an inhibitor of calpains.

Compounds Mimicking NCS1 Expression/Activity

As disclosed above, during WS, the over-degradation of NCS1 induces a severe impairment in the mitochondrial respiratory chain. Thus, without being bound by theory, the inventors believe that reproducing a NCS1 activity, e.g. by using compounds mimicking NCS1 activity, represents an interesting treatment pathway for treating WS.

NCS1 Peptidomimetics

Thus, in a further embodiment, the agonist according to the present invention is a NCS1 peptidomimetic (see e.g. Vagner et al, Curr Opin Chem Biol. 2008 Jun. 12(3): 292-296). The skilled person knows several techniques allowing the design and synthesis of peptidomimetics. Mimetic analogs of the NCS-1 polypeptide or biologically active fragments thereof can be generated by, for example, by substituting the amino acids that are expected to be essential for the biological activity with, e.g., stereoisomers, i.e. D-amino acids (see e.g., Tsukida, J. Med. Chem. 40 (1997), 3534-3541). The structure-based design and synthesis of low-molecular-weight synthetic molecules that mimic the activity of native biological polypeptide is further described in, e.g., Dowd, Nature Biotechnol. 16 (1998), 190-195; Kieber-Emmons, Current Opinion Biotechnol. 8 (1997), 435-441; Moore, Proc. West Pharmacol. Soc. 40 (1997), 115-119; Mathews, Proc. West Pharmacol. Soc. 40 (1997), 121-125; Mukhija, European J. Biochem. 254 (1998), 433-438.

Compounds Stabilizing the NCS1/WFS1 Interaction

As previously disclosed, the inventors have demonstrated that WFS1 interacts with NCS1 thereby preventing the degradation of NCS1 by the proteasome. Thus, stabilizing the NCS1/WFS1 interaction can also represent a very interesting way for preventing the degradation of NCS1 during WS.

Thus, in a further embodiment, the agonist according to the present invention is a compound which stabilizes the WFS1/NCS1 interaction. An example of stabilizer is Lithium.

Methods for Predicting the Severity of Wolfram Syndrome in a Patient

In a further embodiment, the present invention relates to a method for assessing the severity of Wolfram syndrome in a subject comprising the step of measuring the level of NCS1 in a biological sample obtained from said subject, wherein the level of NCS1 is negatively correlated with the severity of WS.

The present inventors have indeed established a correlation between the expression level of NCS1 and the severity of WS.

The term "biological sample" means any biological sample derived from a subject. Examples of such samples include fluids, tissues, cell samples, organs, biopsies, etc. Preferred biological samples are a cell or tissue sample. Typically, the biological sample is a fibroblast sample.

The "NCS1 level" in a sample refers to the concentration of NCS1 in said sample.

Typically, the level of NCS1 measured in the sample obtained from a patient is compared to a control value. Such control value may be determined in regard to the level of NCS1 present in samples taken from one or more healthy subject or to the NCS1 distribution in a control population.

Typically, the lower the level of NCS1 is, the more severe Wolfram syndrome is.

The severity of the WS can be scaled e.g. according to the Wolfram Unified Rating Scale (WURS) (see Nguyen et al, Orphanet J Rare Dis., 7, 89, 2012).

In a particular embodiment, the method for determining if a subject is predisposed to having severe Wolfram syndrome according to the invention is performed after a step of determining whether a patient has WS or not. WS can be diagnosed by any known method by the skilled person, e.g.

by detecting one of the particular mutations of WFS1 disclosed above (see e.g. Strom et al., *Hum. Molec. Genet*, 1998, 7, 2021-2028).

Determination of the NCS1 level can be performed by a variety of methods known by the skilled person for determining the protein level in a sample.

Such methods comprise contacting the sample with a binding partner capable of selectively interacting with the NCS1 present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

ELISA method can be used, wherein the wells of a microtiter plate are coated with an anti-NCS1 antibody. A biological sample to be tested is then added to the coated wells. After a period of incubation sufficient to allow the formation of antibody-antigen complexes, the plate can be washed to remove unbound moieties and a detectably labelled secondary binding molecule added. The secondary binding molecule is allowed to react with any captured sample marker protein, the plate washed and the presence of the secondary binding molecule detected using methods well known in the art.

The present invention will be further disclosed in the following examples.

BRIEF DESCRIPTION OF THE FIGURES

Figure Legends

(A) Co-immunoprecipitation (IP) of Wfs1-myc with Ncs1-Flag with antibody against Flag from lysates of transfected HEK293T.

Immunoprecipitates were analysed by western blotting with antibodies against Flag and myc. Input represents cell lysate. n=3 independent experiments. (B) Transcript levels of WFS1 were quantified by RT-qPCR in control (C1, C2) and patient fibroblasts (P1, P2). The mRNA levels were normalized with reference gene L27. Error bars: SEM n=6 independent experiments. (C) Immunoblot of lysates from controls (C1, C2) and patient fibroblasts (P1, P2) with NCS1 antibody. GAPDH was used as a loading control. The immunoblot bands were quantified by densitometry, and the NCS1/GAPDH ratios were calculated (n=5 independent experiments). (D) Western analysis and quantification of control fibroblasts transfected with scramble siRNA (siScr) or WFS1 siRNA (siWFS1). WFS1 and NCS1 protein expression were analysed 72 h post-siRNA transfection. Data are represented as mean±SEM from n=7 independent experiments *$p<0.05$, using Mann Whitney test. (E) Control and patient cells were treated with 10 μM of MG-132, followed by time course immunoblotting of NCS1.

GAPDH was used as a loading control. Quantification of NCS1 expression level after 16 h of MG-132 treatment normalized to GAPDH is shown. Data are represented as mean±SEM from n=3 independent experiments *$p<0.05$.

Figure 2:
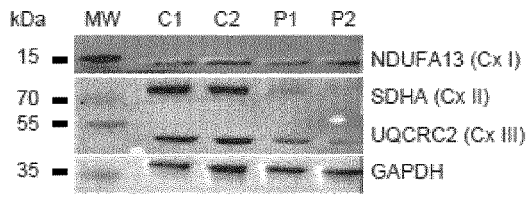
Figure 2:
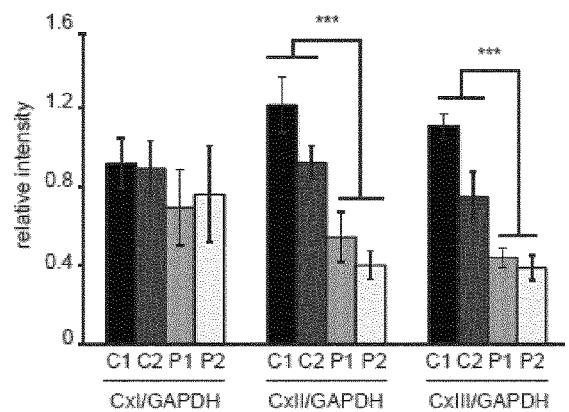
Figure 2:
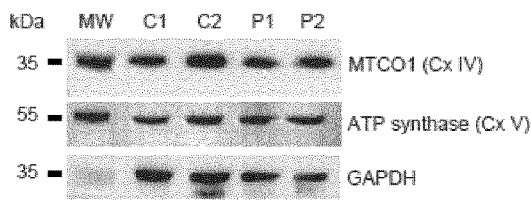
Figure 2:
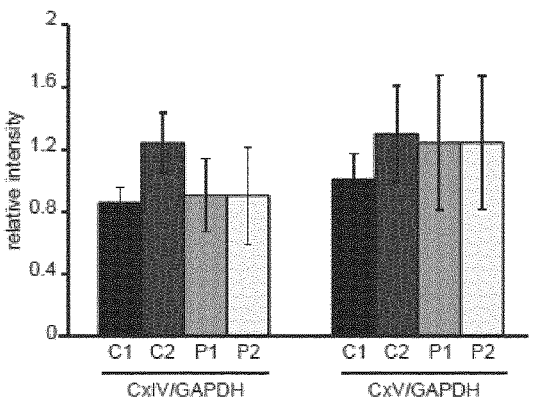
Figure 2:
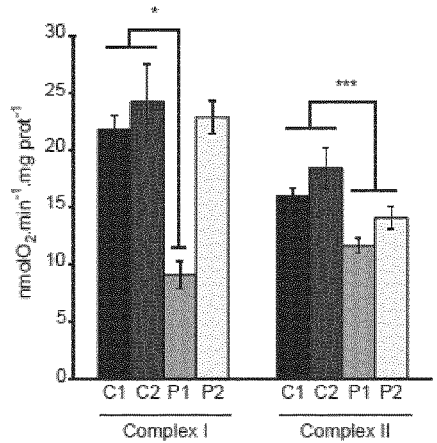
Figure 2:
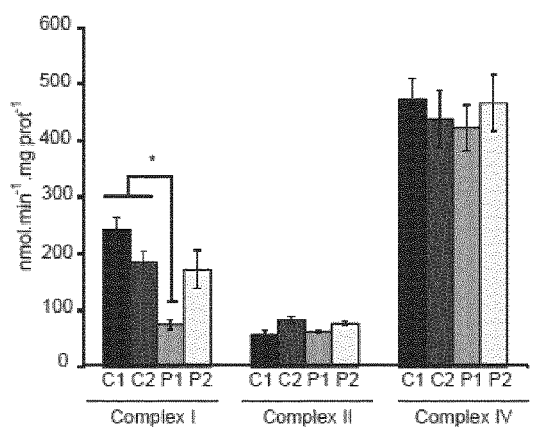

FIG. 2: WFS1 regulates mitochondrial functionality (A) Western blot of NDUFA13 (complex I), SDHA (complex II) and UQCRC2 (complex III) (left) and densitometric analysis (right) in control and patient fibroblasts. GAPDH was used as a loading control. (mean±SEM, n=6) ***$p<0.005$ vs. control. (B) Western blot of MTCO1 (complex IV) and ATPsynthase (complex V) (left) and densitometric analysis (right) in control and patient fibroblasts. GAPDH was used as a loading control. (mean±SEM, n=4). (C) Mitochondrial complex I and complex II-dependent respiratory rate. Respiratory rate: nmol oxygen consumed/min/mg protein. (mean±SEM, n=5 experiments, *$p<0.05$, ***$p<0.005$). (D) Complex I, II and III enzymatic activities in control and patient fibroblasts. (mean±SEM, n=3 experiments, *$p<0.05$).

Figure 3:
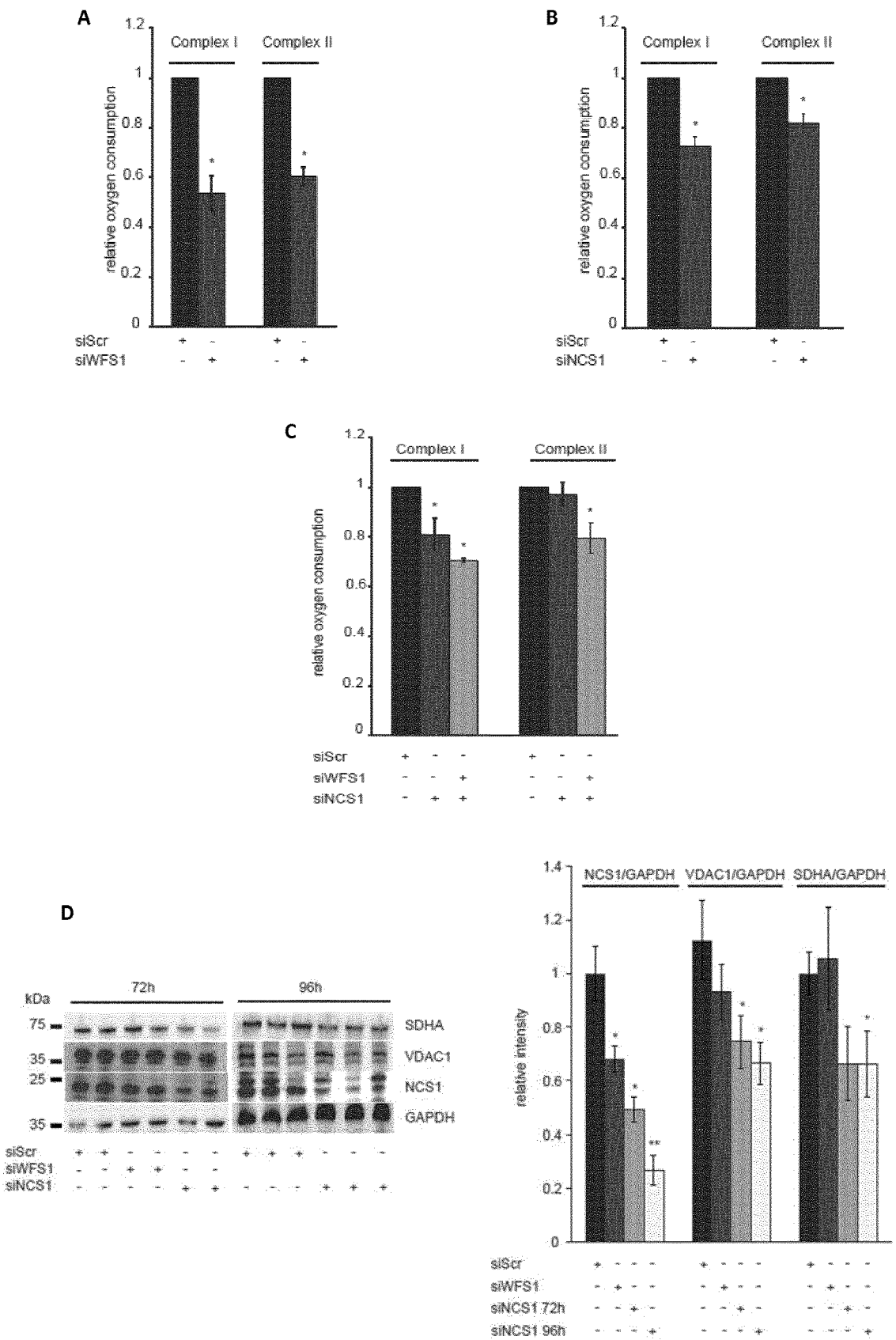

FIG. 3: NCS1 regulates VDAC1 expression and mitochondrial respiratory chain.

(A) Complex I and complex II mediated respiration of control fibroblasts transfected with non-targeting siRNA (siScr) or WFS1 siRNA (siWFS1) (bottom). (mean±SEM, n=7 experiments, *$p<0.05$). (B) Complex I and complex II-mediated respiration of control fibroblasts transfected with non-targeting siRNA (siScr) or NCS1 siRNA (siNCS1) (bottom). (mean±SEM, n=7, *$p<0.05$). (C) Complex I and complex II-mediated respiration of control fibroblasts transfected with nontargeting siRNA (siScr) or NCS1 siRNA (siNCS1) and WFS1 siRNA (siWFS1) (bottom). (mean±SEM, n=3, *$p<0.05$). (D) Effect of NCS1 and WFS1 knockdown on NCS1, VDAC1 and SDHA (complex II) protein expression in control fibroblasts transfected with nontargeting (siScr), NCS1 (siNCS1) or WFS1 (siWFS1) siRNA. NCS1 knockdown effect is shown 72 h and 96 h after siRNA transfection. GAPDH was used as a control of specificity and loading. The immunoblot bands were quantified by densitometry, and the NCS1, VDAC1 and SDHA intensity were calculated (mean±SEM, n=7 experiments, *$p<0.05$, **$p<0.01$).

Figure 4:
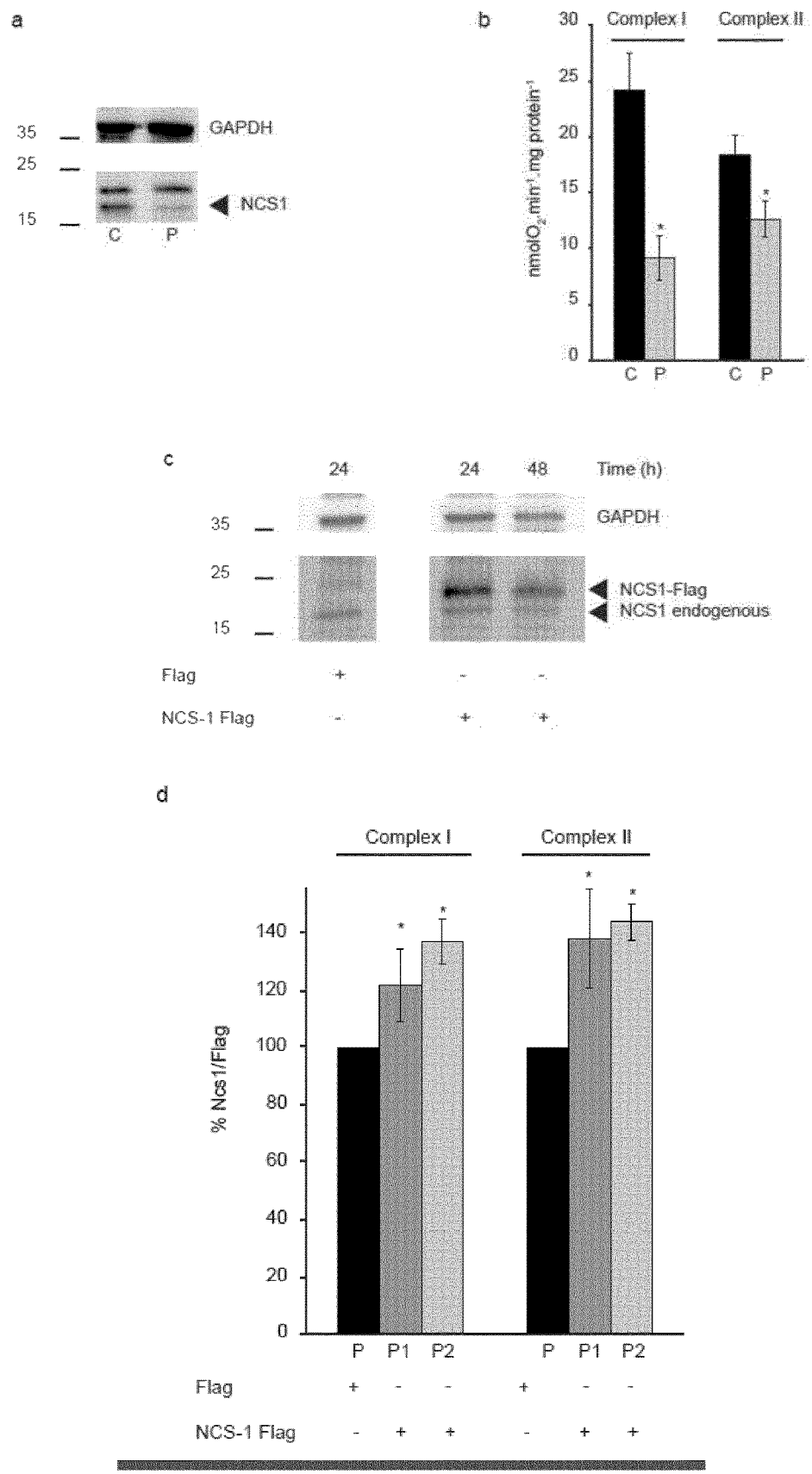

FIG. 4: Overexpression of NCS1 in fibroblasts:

(a) NCS1 expression level in control (C) and WFS1mutant cells (P). (b) represents complex 1 and II respiration rates in controls (C) and in WFS1 mutant cells (P). (c) Overexpression of NCS1 in mutant cells. (d) Represents the complex 1 and II respiration rates in mutant cells transfected either with NCS-1-Flag or with Flag alone.

EXAMPLES

Example 1: The Endoplasmic Reticulum-Mitochondria Crosstalk is Regulated by WFS1/NCS1 Interaction and is Impaired in Wolfram Syndrome Summary Communication between endoplasmic reticulum (ER) and mitochondria plays a pivotal role in calcium (Ca2+) signaling, energy metabolism and cell survival. Dysfunctions of this crosstalk lead to metabolic and neurodegenerative diseases. Wolfram syndrome is a fatal neurodegenerative disease due to mutations of the ER resident protein WFS1. However, clinical phenotype of WS resemble mitochondrial disorders. Here we show that WFS1 forms a complex with NCS1, inositol 1,4,5-triphosphate receptor (ITPR) and voltage-dependent anion channel 1 (VDAC1) to promote ER-mitochondrial Ca2+ transfer. Moreover, we demonstrate that WFS1 associates with NCS1 to prevent its degradation by the proteasome. Finally, we show that NCS1 regulates VDAC expression and mitochondrial respiratory chain. Our results describe an unexpected key role of WFS1 and NCS1 in ER-mitochondria crosstalk and reconcile the ER expression of WFS1 with the mitochondrial phenotype, underlining a novel pathogenic mechanism for WS and opening new insights into the biogenesis of other neurodegenerative diseases.

Introduction

Mitochondria exert essential cellular functions, from bioenergetics and metabolism to ion homeostasis and apoptosis. Mitochondrial dysfunction has been linked to many of the most common neurodegenerative disorders that are disabling and often fatal diseases. However, the cause of mitochondrial dysfunction remains largely undefined. It is well known that mitochondria interacts physically and functionally with endoplasmic reticulum (ER) via mitochondria-associated membranes (MAM) (Csordas et al., 2006) to influence cellular physiology and viability (Giorgi et al., 2015). Interestingly, the study of MAM has begun to be recognized as a contributor to neurodegeneration.

Loss of function of the ER protein Wolfram Syndrome 1 (WFS1) leads to a neurodegenerative disease associated with diabetes, optic atrophy and deafness (Barrett et al., 1995) called Wolfram syndrome. WS was originally described as a mitochondriopathy due to a clinical phenotype resembling other mitochondrial disorders (Bundey et al., 1993). However, this hypothesis has been challenged by studies showing an ER distribution of WFS1 (Takeda et al., 2001). Here we report a previously unknown function of WFS1 in mitochondrial functionality supporting the notion that WS is in part a mitochondrial disorder.

Our results reveal that WFS1 is essential to guarantee ER-mitochondria Ca2+ transfer and bioenergetics via its interaction with Neuronal Calcium Sensor 1 (NCS1), a Ca2+ binding protein. This study shows that WFS1 and NCS1 may participate to the tethering of ER to mitochondria and may contribute to neurodegeneration.

Results and Discussion

WFS1 Iteracts with and Modulates the Expression of NCS1

Figure 1:
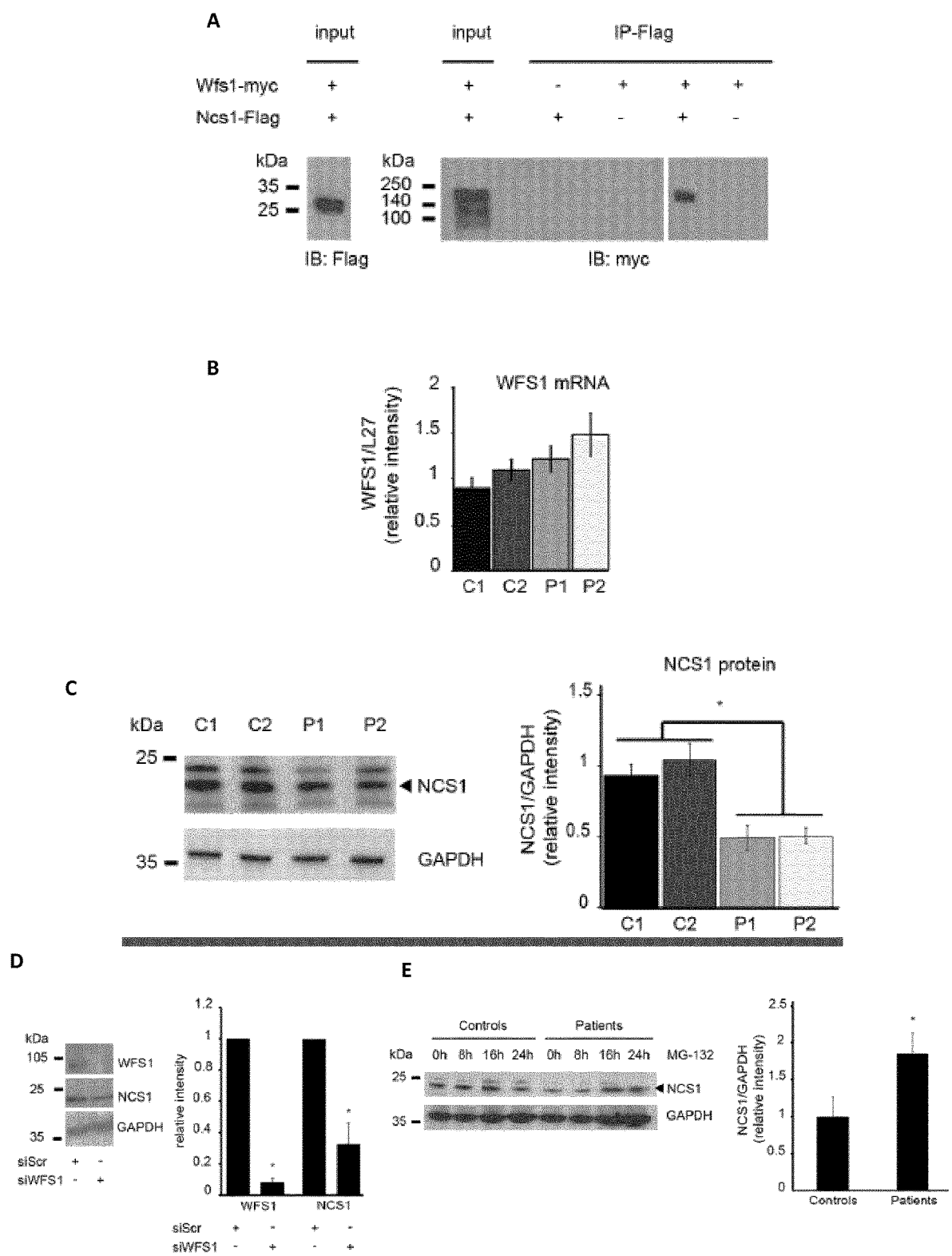
FIG. 1: WFS1 interacts with and modulates the expression of NCS1

To gain insight into how the loss of function of the ER protein WFS1 induces mitochondriopathy, we sought to identify protein partners of the cytosolic part of WFS1. We performed a yeast two-hybrid analysis using residues 1-311 of murine Wfs1 as bait and identified mouse Ncs1 as an interacting partner (Data not shown). NCS1 is an EF-hand cytosolic protein preferentially expressed in neurons (Pongs et al., 1993) and known to regulate inositol 1,4,5-triphosphate receptor (ITPR) (Nakao et al., 2015; Schlecker et al., 2006; Zhang et al., 2014) and Dopamine D2 receptor (Kabbani et al., 2002). To confirm Wfs1/Ncs1 interaction, we performed a co-immunoprecipitation assay. We showed that Wfs1-myc coimmunoprecipitates with Ncs1-Flag from HEK293T cell lysates (FIG. 1A). This association identifies a novel WFS1 neuronal interacting protein that may play an important role in WS.

To investigate NCS1 functions in WS, we took advantage of WFS1-null patient fibroblasts. The patients carried two predicted loss-of-function alleles in WFS1 (V509-Y513del and F882fsX950) and exhibit typical WS. We first examined the expression of WFS1 using quantitative PCR and western blot. No difference in the mRNA expression level of WFS1 between controls and patients were observed (FIG. 1B). In contrast, the WFS1 protein expression level was decreased in patients (Data not shown). We confirmed this decrease using immunocytochemistry. These results suggest that WFS1 loss of function mutations impacted the production/stability of the protein rather than the expression/stability of the mRNA. This is in good agreement with previous results showing a decrease stability of mutant WFS1 protein over-expressed in COS-7 cells (Hofmann and Bauer, 2006; Hofmann et al., 2003). Then, we analysed NCS1 mRNA and protein expression in patient cells. Similarly, mRNA levels were unchanged between controls and patients (Data not shown), whereas NCS1 protein level was decreased by almost 50% in patient fibroblasts (FIG. 1C). Consistent with this observation, knock down of WFS1 using siRNA in control fibroblasts decreased NCS1 protein level by 60% (FIG. 1D). These results suggested that WFS1 may regulate NCS1 protein stability. Accordingly, WFS1 has been described as a key regulator of ATF6a level in stabilizing HRD1 (Fonseca et al., 2010) as well as a regulator of SERCA expression (Zatyka et al., 2014) especially through the ubiquitin proteasome pathway. Therefore, to determine whether WFS1 affect NCS1 expression level involves the proteasome, we used the proteasome inhibitor MG-132. Interestingly, after 16 h of MG-132 treatment, we observed a two-fold increase in NCS1 expression in patient fibroblasts (FIG. 1E) whereas in control cells MG-132 was ineffective. Altogether, these results indicate that WFS1 may protect NCS1 from proteasomal degradation.

WFS1 Interacts with ITPR and Regulates Mitochondrial Ca2+ Uptake

WFS1 is thought to play a role in Ca2+ homeostasis by negatively regulating SERCA turnover and modifying the filling state of the ER Ca2+ store (Takei et al., 2006; Zatyka et al., 2014). Moreover, as NCS1 modulates the ER Ca2+ release channel, the inositol 1,4,5-triphosphate receptor (ITPR) (Iketani et al., 2009; Schlecker et al., 2006), we hypothesized that WFS1, NCS1 and ITPR may form a complex to modulate Ca2+ flux. To test this hypothesis, we performed co-immunoprecipitation experiments. We first confirmed the interaction of mouse Ncs1 with ITPR receptor in HEK293T (Data not shown). Then, we demonstrated the interaction of mouse Wfs1 with ITPR (Data not shown). These interactions are consistent with a possible WFS1, ITPR and NCS1 complex formation. We then measured the effect of WFS1 loss of function in Ca2+ flux. Cytoplasmic (Fluo-4) and mitochondrial (Rhod-2) [Ca2+] were imaged by confocal microscopy on fibroblasts after histamine stimulation, known to induce Ca2+ release from ER stores. Histamine triggered similar IP3-mediated cytosolic [Ca2+] elevations in both control and patient cells, whereas mitochondrial Ca2+ uptake was significantly diminished in patients (Data not shown). We next measured mitochondrial membrane potential (Δψm) using TMRM dye in control and patient cells. The mitochondrial uncoupler FCCP was applied to dissipate Δψm. No significant difference was observed on FCCP-induced TMRM fluorescence decreased in both groups indicating a similar Δψm. Therefore, the lack of mitochondrial Ca2+ uptake in patient cells was not due to a smaller driving force. These results demonstrated that WFS1 physically associates with ITPR and is necessary for ITPR-mediated mitochondrial Ca2+ uptake.

Crosstalk between ER and mitochondria is essential for the normal functioning of eukaryotic cells. This inter-organelle communication between the ER and mitochondria is crucial for processes such as lipid synthesis and transport (Vance, 2014), mitochondrial functions (van Vliet et al., 2014), regulation of Ca2+ homeostasis (Patergnani et al., 2011), autophagy (Marchi et al., 2014) and apoptosis (Grimm, 2012). ER directly communicates with mitochondria through close contacts referred to as mitochondria-associated membranes (MAMs), which are micro-domains allowing an efficient Ca2+ transfer between the ER to the mitochondria and maintaining cellular metabolism and survival. Ca2+ transfer from the ER into the mitochondria is facilitated by proteins, which tether the two organelles together. For example, the ITPR on the ER interacts with VDAC1 on the outer mitochondrial membrane through the molecular chaperone glucose-regulated protein, GRP75 (Szabadkai et al., 2006).

The ITPR/GRP75/VDAC1 complex also involves the mitochondrial Ca2+ uniporter (MCU) on the inner mitochondrial membrane (IMM) (Szabadkai et al., 2006) to allow Ca2+ transfer from the ER to mitochondria. Therefore, we asked if the complex ITPR/GRP75/VDAC1 and MCU were affected in Wolfram patient cells. This was first assessed by examining the expression of these proteins. There was a marked down-regulation in the expression of proteins involved in mitochondrial Ca2+ uptake such as VDAC1 in patient fibroblasts. MCU was also decreased in the most affected patient P1. No significant differences were found in GRP75 and ITPR expression. Thus, we revealed that loss of WFS1 may down regulates VDAC1 and MCU expression and impairs mitochondrial Ca2+ uptake, possibly through down-expression of NCS1.

WFS1 Regulates Mitochondrial Functionality

Reduced mitochondrial Ca2+ uptake might adversely affect various metabolic pathways, resulting in altered energy production. We then evaluated some key enzymes reflecting mitochondrial function, including Citrate Synthase (CS) and respiratory complexes. CS activity was decreased in the mutant cells (25%) when normalized to protein content suggesting abnormal mitochondrial integrity. Therefore, we measured the protein expression level of selected subunits of each complex in the mitochondrial electron transport chain. Patient cells presented a decrease in the expression of complex II (SDHA) and complex III (UQCRC2) subunits (FIG. 2A). The expression level of complex I (NDUFA13), complex IV (MTCO1) and complex V (ATP synthase) subunits did not differ between controls and patients (FIG. 2A-2B). These results indicated that there might be a selective loss of mitochondrial proteins. We wondered whether such a decrease could impact mitochondrial bioenergetics. We thus evaluated Oxidative Phosphorylation System (OXPHOS) with oxygen consumption and enzymatic activity of complexes. Both WFS1 mutant cells exhibited a significant decrease (20%) of complex II driven respiration (FIG. 2C). Moreover, the patient P1 showed a three-fold diminution of complex I respiration rate (FIG. 2C). To get deeper insights into the cause of the observed decreased mitochondrial respiration in patient fibroblasts, the activities of respiratory chain complexes I (NADH ubiquinone reductase), II (succinate ubiquinone reductase) and IV (cytochrome c oxidase) were specifically assessed on cell lysates. The activity of complex I was significantly threefold decreased in patient P1 only, whereas the activity of complex II and IV were unchanged in all patient cells as compared with controls (FIG. 2D). Together, these results demonstrated that in Wolfram patients, altered respiration of complex II is linked to the depletion of the complex II amount whereas in the most affected patient P1 the decrease of complex I respiration rate reflected a loss of respiratory capacity. We next assessed cell death sensitivity in Wolfram patients' cells. Cells proliferation under galactose was reduced by 30% at 72 h in patient cells and apoptosis induced by tert-butylhydroperoxyde (tBHP), an activator of mitochondrial apoptosis pathway, was increased in patient cells compared to controls. These results confirm that mitochondrial functionality is impaired in patient fibroblasts resulting in apoptosis sensitivity of the cells. Yet, no autophagy was observed using biochemical markers as LC3BII/LC3BI ratio and Beclin.

NCS1 Regulates VDAC1 Expression and Mitochondrial Respiratory Chain

To elucidate the differential roles of WFS1 and NCS1 on mitochondrial functionality, we used short interfering RNAs (siRNAs) to deplete human fibroblasts of either WFS1 or NCS1. SiRNAs efficiently suppressed WFS1 and NCS1 expression 72 h and 96 h post-transfection respectively. Single knockdown of either WFS1 or NCS1 led to a noticeable decline in both complex I- and complex II-driven respiration as observed in patient fibroblasts (FIG. 3A-3B). Mitochondrial respiration was more affected with WFS1 siRNAs due to the partial knockdown of NCS1 associated to the decrease of WFS1 expression (FIG. 1D). Interestingly, double knockdown of WFS1 and NCS1 induced a decrease of respiration 24 h before NCS1 knockdown alone (FIG. 3C). This result suggests that WFS1 and NCS1 share the same signaling pathway and that the loss of WFS1 could precipitate the decrease of NCS1 and the mitochondrial dysfunction associated. We then examined whether WFS1 or NCS1 knockdown affect VDAC1 and SDHA (complex II) expression. In NCS1 knockdown cells, VDAC1 and SDHA expression were significantly reduced compared to controls (FIG. 3D). In contrast, WFS1 knockdown did not affect VDAC1 and SDHA expression (FIG. 3D). This result demonstrated that NCS1 knockdown could down-regulate VDAC1 and be a key determinant for the maintenance of mitochondrial function.

Based upon the data provided, we proposed a novel mechanism for WS. WFS1, NCS1 and ITPR may consist of a complex of proteins associated with ER-mitochondria contact sites. In healthy cells, WFS1 interacts with NCS1 and prevent its degradation by the proteasome. The complex WFS1/NCS1/ITPR is functional and Ca2+ can transfer from ER to mitochondria properly and activate the tricarboxylic acid cycle (TCA cycle) and mitochondrial respiratory chain. When WFS1 is lost, the complex WFS1/NCS1/ITPR is disorganized and NCS1 is partially degraded by the proteasome. Consequently, altered ER-mitochondrial Ca2+ transfer leads to mitochondrial bioenergetic dysfunction that can results in the activation of cell death.

Importantly, here we demonstrate for the first time an unknown link between WFS1 and NCS1 that is critical for mitochondrial functionality.

Previously, WS studies focused on diabetes because the lack of WFS1 causes pancreatic beta cell dysfunction and death (Fonseca et al., 2005; Ishihara et al., 2004; Riggs et al., 2005). However, diabetes is efficiently treated by insulin supplement, whereas neuronal death in brain, cerebellum and sensory organs is life threatening and unavoidably causes blindness, deafness and death. The identification of NCS1, a Ca2+ binding protein expressed predominantly in neurons, is likely to be involved the pathophysiological mechanisms of neuronal defects, possibly different from those in play in the pancreas. It is striking that WS symptoms resemble those encountered in mitochondrial disorders. Yet, until now, no biochemical evidence supported the notion that part of this syndrome was related to mitochondrial dysfunction. The present findings of absent mitochondrial Ca2+ uptake and abnormal respiratory functions demonstrate that WS is in part a mitochondrial disorder, in line with the optic atrophy and deafness which are frequently found in mitochondriopathies.

Experimental Procedures

Detailed methods are in Supplemental Experimental Procedures.

Ethical Approval:

The research studies on patient cell lines were approved by the ethical standards of the institutional research committee (#11018S) and with the 1964 Helsinki declaration.

Cell Cultures

Fibroblasts were cultured from skin biopsies taken after obtaining informed consent from three controls and two affected patients carrying mutations in WFS1 gene as previously described (Angebault et al., 2011).

siRNA and Transfection

Control fibroblasts were transfected with siRNA directed against WFS1 and/or with siRNA directed against NCS1 (Thermo Fisher Scientific Biosciences, ON-TARGET plus Human NCS1 siRNA SMART pool). Transfection with an ON-TARGET non targeting pool (siScramble) was used as controls.

Immunofluorescence (IF)

Cells were fixed using 4% PFA and permeabilised using a blocking solution containing 0.1% Triton X-100 and 5% donkey serum in PBS. Rabbit polyclonal antibody WFS1 (1:250, Cell Signalling) was incubated overnight at 4° C.

Real-Time RT-PCR

Real-time PCR were performed on total RNA extracted from cells using the RNeasy Mini Kit (Qiagen) and reverse-transcribed with the SuperScript III First Strand Kit (Invitrogen) according to the manufacturer's instructions.

Enzymatic activities and Oxygen consumption

The activity of the mitochondrial respiratory chain complexes and respiratory rates were measured on cell homogenates as described previously (Angebault et al., 2011).

Western Blot Analysis

Level of proteins were detected by immunoblot using commercially available antibodies, revealed using chemiluminescence.

Co-Immunoprecipitation (Co-IP)

For the co-IP studies, HEK293T were transfected with Wfs1-myc, Ncs-1-Flag and Itpr1 using Lipofectamine 2000 according to the manufacturer's instructions.

Yeast Two-Hybrid

Yeast two-hybrid screening was performed by Hybrigenics Services, S.A.S., Paris, France.

Confocal Imaging

Rhod-2 AM (3 µM, Molecular Probes) was used to measure mitochondrial Ca2+. To measure cytosolic Ca2+ fibroblasts were loaded with fluo-4 AM (5 µM, Molecular Probes). To measure mitochondrial membrane potential ($\Delta\psi m$), fibroblasts were loaded with 10 nM TMRM (Life technologies).

Statistical Aanalysis

The non-parametric Mann-Whitney U test was used to compare the fibroblasts from WFS1 patients and controls. Differences were considered significant at $p<0.05$*, $p<0.01$ and $p<0.005$*.

REFERENCES

Angebault, C., Gueguen, N., Desquiret-Dumas, V., Chevrollier, A., Guillet, V., Verny, C., Cassereau, J., Ferre, M., Milea, D., Amati-Bonneau, P., et al. (2011). Idebenone increases mitochondrial complex I activity in fibroblasts from LHON patients while producing contradictory effects on respiration. BMC research notes 4, 557.

Barrett, T. G., Bundey, S. E., and Macleod, A. F. (1995). Neurodegeneration and diabetes: UK nationwide study of Wolfram (DIDMOAD) syndrome. Lancet 346, 1458-1463.

Bundey, S., Fielder, A., and Poulton, K. (1993). Wolfram syndrome: mitochondrial disorder. Lancet 342, 1059-1060.

Csordas, G., Renken, C., Varnai, P., Walter, L., Weaver, D., Buttle, K. F., Balla, T., Mannella, C. A., and Hajnoczky, G. (2006). Structural and functional features and significance of the physical linkage between ER and mitochondria. The Journal of cell biology 174, 915-921.

Fonseca, S. G., Fukuma, M., Lipson, K. L., Nguyen, L. X., Allen, J. R., Oka, Y., and Urano, F. (2005). WFS1 is a novel component of the unfolded protein response and maintains homeostasis of the endoplasmic reticulum in pancreatic beta-cells. The Journal of biological chemistry 280, 39609-39615.

Fonseca, S. G., Ishigaki, S., Oslowski, C. M., Lu, S., Lipson, K. L., Ghosh, R., Hayashi, E., shihara, H., Oka, Y., Permutt, M. A., and Urano, F. (2010). Wolfram syndrome 1 gene negatively regulates ER stress signaling in rodent and human cells. The Journal of clinical investigation 120, 744-755.

Giorgi, C., Missiroli, S., Patergnani, S., Duszynski, J., Wieckowski, M. R., and Pinton, P. (2015). Mitochondria-associated membranes: composition, molecular mechanisms, and physiopathological implications. Antioxidants & redox signaling 22, 995-1019.

Grimm, S. (2012). The ER-mitochondria interface: the social network of cell death. Biochim Biophys Acta 1823, 327-334 .

Hofmann, S., and Bauer, M. F. (2006). Wolfram syndrome-associated mutations lead to instability and proteasomal degradation of wolframin. FEBS letters 580, 4000-4004.

Hofmann, S., Philbrook, C., Gerbitz, K. D., and Bauer, M. F. (2003). Wolfram syndrome: structural and functional analyses of mutant and wild-type wolframin, the WFS1 gene product. Human molecular genetics 12, 2003-2012.

Iketani, M., Imaizumi, C., Nakamura, F., Jeromin, A., Mikoshiba, K., Goshima, Y., and Takei, K. (2009). Regulation of neurite outgrowth mediated by neuronal calcium sensor-1 and inositol 1,4,5-trisphosphate receptor in nerve growth cones. Neuroscience 161, 743-752.

Ishihara, H., Takeda, S., Tamura, A., Takahashi, R., Yamaguchi, S., Takei, D., Yamada, T., Inoue, H., Soga, H., Katagiri, H., et al. (2004). Disruption of the WFS1 gene in mice causes progressive beta-cell loss and impaired stimulus-secretion coupling in insulin secretion. Human molecular genetics 13, 1159-1170.

Kabbani, N., Negyessy, L., Lin, R., Goldman-Rakic, P., and Levenson, R. (2002). Interaction with neuronal calcium sensor NCS-1 mediates desensitization of the D2 dopamine receptor. J Neurosci 22, 8476-8486.

Marchi, S., Patergnani, S., and Pinton, P. (2014). The endoplasmic reticulum-mitochondria connection: one touch, multiple functions. Biochim Biophys Acta 1837, 461-469.

Nakao, S., Wakabayashi, S., and Nakamura, T. Y. (2015). Stimulus-dependent regulation of nuclear Ca2+ signaling in cardiomyocytes: a role of neuronal calcium sensor-1. PloS one 10, e0125050.

Nguyen C, Foster E R, Paciorkowski A R, Viehoever A, Considine C, Bondurant A, Marshall B A, Hershey T; Washington University Wolfram Study Group. Reliability and validity of the Wolfram Unified Rating Scale (WURS). Orphanet J Rare Dis. 2012 Nov. 14; 7:89.

Patergnani, S., Suski, J. M., Agnoletto, C., Bononi, A., Bonora, M., De Marchi, E., Giorgi, C., Marchi, S., Missiroli, S., Poletti, F., et al. (2011). Calcium signaling around Mitochondria Associated Membranes (MAMs). Cell Commun Signal 9, 19.

Pongs, O., Lindemeier, J., Zhu, X. R., Theil, T., Engelkamp, D., Krah-Jentgens, I., Lambrecht, H. G., Koch, K. W., Schwemer, J., Rivosecchi, R., and et al. (1993). Frequenin a novel calcium-binding protein that modulates synaptic efficacy in the Drosophila nervous system. Neuron 11, 15-28.

Riggs, A. C., Bernal-Mizrachi, E., Ohsugi, M., Wasson, J., Fatrai, S., Welling, C., Murray, J., Schmidt, R. E., Herrera, P. L., and Permutt, M. A. (2005). Mice conditionally lacking the Wolfram gene in pancreatic islet beta cells exhibit diabetes as a result of enhanced endoplasmic reticulum stress and apoptosis. Diabetologia 48, 2313-2321.

Schlecker, C., Boehmerle, W., Jeromin, A., DeGray, B., Varshney, A., Sharma, Y., Szigeti-Buck, K., and Ehrlich, B. E. (2006). Neuronal calcium sensor-1 enhancement of InsP3 receptor activity is inhibited by therapeutic levels of lithium. The Journal of clinical investigation 116, 1668-1674.

Szabadkai, G., Bianchi, K., Varnai, P., De Stefani, D., Wieckowski, M. R., Cavagna, D., Nagy, A. I., Balla, T., and Rizzuto, R. (2006). Chaperone-mediated coupling of endoplasmic reticulum and mitochondrial Ca2+ channels. The Journal of cell biology 175, 901-911.

Takeda, K., Inoue, H., Tanizawa, Y., Matsuzaki, Y., Oba, J., Watanabe, Y., Shinoda, K., and Oka, Y. (2001). WFS1 (Wolfram syndrome 1) gene product: predominant subcellular localization to endoplasmic reticulum in cultured cells and neuronal expression in rat brain. Human molecular genetics 10, 477-484.

Takei, D., Ishihara, H., Yamaguchi, S., Yamada, T., Tamura, A., Katagiri, H., Maruyama, Y., and Oka, Y. (2006). WFS1 protein modulates the free Ca(2+) concentration in the endoplasmic reticulum. FEBS letters 580, 5635-5640.

van Vliet, A. R., Verfaillie, T., and Agostinis, P. (2014). New functions of mitochondria associated membranes in cellular signaling. Biochim Biophys Acta 1843, 2253-2262.

Vance, J. E. (2014). MAM (mitochondria-associated membranes) in mammalian cells: lipids and beyond. Biochim Biophys Acta 1841, 595-609.

Zatyka, M., Da Silva Xavier, G., Bellomo, E. A., Leadbeater, W., Astuti, D., Smith, J., Michelangeli, F., Rutter, G. A., and Barrett, T. G. (2014). Sarco(endo)plasmic reticulum ATPase is a molecular partner of Wolfram syndrome 1 protein, which negatively regulates its expression. Human molecular genetics.

Zhang, S. X., Sanders, E., Fliesler, S. J., and Wang, J. J. (2014). Endoplasmic reticulum stress and the unfolded protein responses in retinal degeneration. Experimental eye research 125, 30-40.

Example 2: Overexpression of NCS1 Allows Increasing Complex II Driven Respiration in WS Cells Fibroblasts of patient's were electropored with Flag alone or Ncs-1-Flag using basic Fibroblasts Nucleofector kit (Lonza) according to the manufacturer's instructions and processed 24 hours later. Ncs1 was sub-cloned into C-terminal p3XFLAG-CMV between EcoR1 and BamH1.

In mutant cells, NCS1 expression level is decreased by 50% (FIG. 4a). WFS1 mutant cells exhibited a significant decrease (20%) of complex II driven respiration (FIG. 4b) and a three-fold diminution of complex I respiration rate (FIG. 4b). The overexpression of NCS1 in mutant cells (FIG. 4c) leads to a 30% increased of complex I driven respiration and 40% increased of complex II driven respiration compared to Flag alone (FIG. 4d) 24 h after the transfection.

The invention claimed is:

1. A method for the treatment of Wolfram Syndrome (WS), comprising administering, to a patient in need thereof, a therapeutically effective amount of an agonist of the neuronal calcium sensor 1 (NCS1), wherein said agonist is an NCS1-encoding polynucleotide.

\* \* \* \* \*